US00PP24300P2

(12) United States Plant Patent
Podaras

(10) Patent No.: US PP24,300 P2
(45) Date of Patent: Mar. 11, 2014

(54) ***BUDDLEIA* PLANT NAMED 'HINEBUD3'**

(50) Latin Name: ***Buddleia* hybrid**
Varietal Denomination: Hinebud3

(75) Inventor: Peter C. Podaras, Davis, CA (US)

(73) Assignee: Hines Growers, Inc., Fallbrook, CA (US)

( * ) Notice: Subject to any disclaimer, the term of this patent is extended or adjusted under 35 U.S.C. 154(b) by 0 days.

(21) Appl. No.: 13/573,317

(22) Filed: Sep. 10, 2012

(51) Int. Cl.
*A01H 5/00* (2006.01)

(52) U.S. Cl.
USPC ..... Plt./242

(58) Field of Classification Search
USPC ..... Plt./242
See application file for complete search history.

*Primary Examiner* — Kent L Bell

(74) *Attorney, Agent, or Firm* — Barbara Campbell; Cochran Freund & Young LLC

(57) ABSTRACT

A *Buddleia* plant particularly distinguished by low-growing and densely branched, large, pure-white inflorescences that flower soon after propagation, and dark foliage, is disclosed.

2 Drawing Sheets

Genus and species: *Buddleia* hybrid (complex hybrid of *Buddleia davidii*×*Buddleia alternifolia*×*Buddleia caryopterifolia*×*Buddleia lindleyana*×*Buddleia crispa*).

Variety denomination: 'Hinebud3'.

BACKGROUND OF THE NEW PLANT

The present invention comprises a new and distinct variety of *Buddleia*, botanically known as *Buddleia* hybrid, and hereinafter referred to by the variety name 'Hinebud3'. The new variety originated from a cross-pollination conducted in Winters, Calif. in August 2010 between the female *Buddleia* parent, an un-named seedling (unpatented) and the male *Buddleia* parent, an un-named seedling (unpatented). A single plant selection was subsequently chosen for further evaluation and asexual propagation in Winters, Calif.

The new plant was first asexually propagated in June 2011 in Winters, Calif. and has been asexually reproduced by cuttings for two years in Winters, Calif. The present invention has been found to retain its distinctive characteristics through successive asexual propagations by softwood cuttings.

'Hinebud3' has not been made publicly available or sold more than one year prior to the filing of this application.

SUMMARY OF THE INVENTION

The following are the most outstanding and distinguishing characteristics of the new variety when grown under normal horticultural practices in Winters, Calif.

1. Low-growing and densely branched;
2. Large, pure-white inflorescences that flower soon after propagation; and
3. Dark foliage.

DESCRIPTION OF THE PHOTOGRAPHS

This new *Buddleia* plant is illustrated by the accompanying photographs which show the overall plant habit, foliage and inflorescence of the plant. The colors are as true as can be reasonably obtained by conventional photographic procedures. The photographs are of a 15-month-old plant grown in a greenhouse and outdoors in Winters, Calif. in May 2012.

DESCRIPTION OF THE NEW VARIETY

Figure 1:
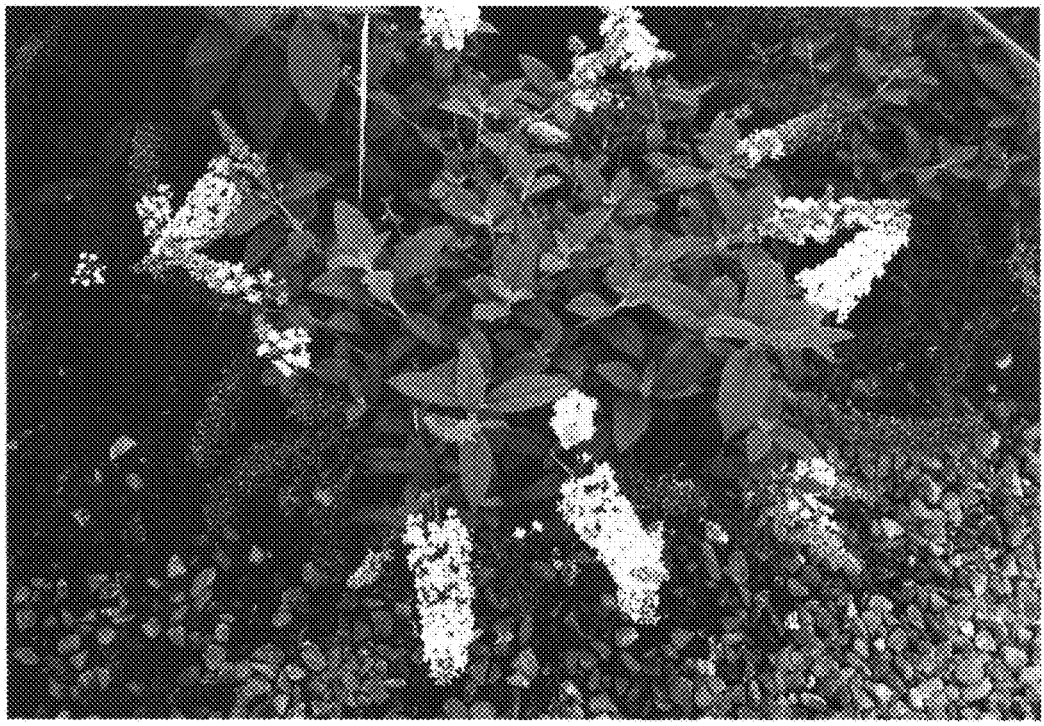
FIG. 1 shows the whole plant, including the habit, foliage and inflorescence.
Figure 2:
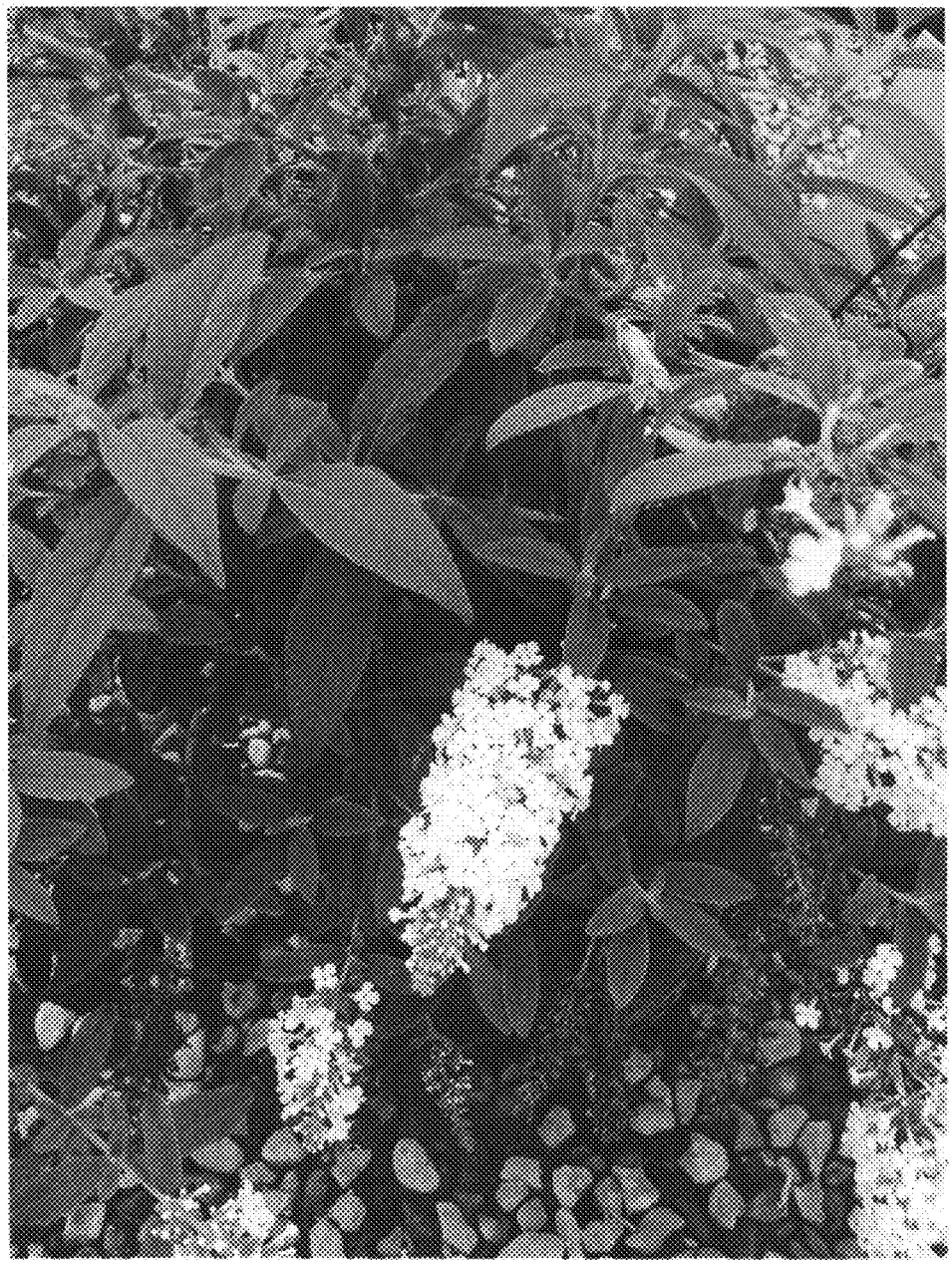
FIG. 2 shows a close-up of the inflorescence and foliage.

The following detailed descriptions set forth the distinctive characteristics of 'Hinebud3'. The data which defines these characteristics were collected from asexual reproductions carried out in Winters, Calif. The plant history was taken in May 2012 on two-year old plants grown outdoors in Winters, Calif. Color references were taken under natural light and are to The R.H.S. Colour Chart of The Royal Horticultural Society of London (R.H.S.), fifth edition (2007) or to the The R.H.S. mini chart (2005) as indicated. Texture descriptions were taken using a dissecting microscope.

DESCRIPTION OF THE NEW PLANT

Classification:

*Family.*—Scrophulariaceae.

*Botanical name.*—*Buddleia* hybrid (complex hybrid of *Buddleia davidii*×*Buddleia alternifolia*×*Buddleia caryopterifolia*×*Buddleia lindleyana*×*Buddleia crispa*).

*Common name.*—Butterfly bush.

*Denomination.*—'Hinebud3'.

Plant:

*Form.*—Bush, oval-shaped.

*Habit.*—Compact, well-branched shrub.

*Height* (*measured from the top of the soil*).—122.0 cm.

*Width* (*horizontal plant diameter*).—135.0 cm.

*Time to produce a finished plant.*—12 weeks from a softwood cutting.

*Outdoor plant performance.*—Prefers full sun, USDA zones 5-9.

*Time to initiate and develop roots.*—About 8 to 10 days.

*Root description and habit.*—White (RHS 155B), fibrous, dense and branching.

*Propagation type.*—Softwood cuttings.

Lateral branches:

*Quantity per plant.*—Approximately 80.

*Length.*—About 50.0 cm to 60.0 cm.

*Internode length.*—3.0 cm.

*Diameter (from midpoint).*—About 0.5 cm to 0.7 cm.

*Color.*—RHS 139C.

*Strength.*—Strong and somewhat flexible.

*Texture.*—Tomentose.

*Anthocyanin.*—Absent.

Leaves:

*Quantity of leaves per branch.*—About 16 to 24.

*Arrangement.*—Opposite.

*Length.*—10.0 cm to 12.0 cm.

*Width.*—3.0 cm to 3.6 cm.

*Shape.*—Lanceolate.

*Apex.*—Acuminate.

*Base.*—Attenuate.

*Margin.*—Serrate.

*Color, immature.*—Upper surface: RHS 139A. Lower surface: RHS 191C.

*Color, mature.*—Upper surface: RHS 139A. Lower surface: RHS 191B.

*Texture.*—Upper surface: Mostly glabrous but with scattered stellate trichomes. Lower surface: Densely floccose with stellate trichomes.

*Venation type.*—Arcuate.

*Venation color.*—Upper surface: RHS 138D. Lower surface: RHS 138C.

*Petiole.*—Color: RHS 138C. Length: 0.2 cm. Diameter: 0.16 cm. Texture: Floccose.

Inflorescence:

*Height.*—18.0 cm to 20.0 cm.

*Width.*—8.0 cm to 10.0 cm.

*Bud.*—Color: RHS N999 (using The R.H.S. mini color chart) at top and RHS 11C along the corolla. Shape: Tetragonal. Height: 1.0 cm from calyx to tip. Diameter: 0.175 cm.

*Flower.*—Type and habit: Single and salverform shaped flowers arranged in compound terminal panicles; flowers face upright and outward; panicles are roughly conical in shape; branching is thyrse, up to four times on the basal half. Fragrance: Sweet and pleasant. Flowering season: May to September in USDA zones 5-9; continuous all year in USDA zones 10-11. Lastingness of inflorescence on the plant: About 10 to 14 days. Depth: 0.4 cm to 0.5 cm. Width: 0.8 cm. Quantity per inflorescence: 1100 to 1500. Petals: Arrangement and quantity per flower: Four arranged in a single whorl but occasionally, there are 5 petals on flowers on the distal portion of the inflorescence; the petals fused into a narrow tube; the petals are flat allowing the inside of the corolla to be visible. Length: 0.4 cm (from the top of the fused corolla, the corolla length is 1.1 cm). Width: 1.0 cm. Shape: Rounded. Apex: Obtuse. Base: Fused into the corolla tube. Margin: Crenate. Texture: Upper surface: Papillate with hispid trichomes at the base going down into the inside of the corolla. Lower surface: Less ocpillate than surface with scattered clusters of stellate trichomes along the outer margin. Color, when opening (using The R.H.S. mini color chart): Upper surface: RHS 999D. Lower surface: RHS 999D. Color, when open (using The R.H.S. mini color chart): Upper surface: RHS 999D. Lower surface: RHS 999D. Tube: Length: 1.1 cm. Width: 0.2 cm to 0.13 cm at the base. Color: Inside: RHS 155D. Outside: RHS 157B. Texture: Inside: Setose hairs perpendicular to the surface. Outside: Papillate with downward pointing strigose trichomes. Calyx: Arrangement and quantity: Four sepals arranged in a single whorl and fused towards the base. Shape: Tubular, appressed to the corolla tube. Sepals: Length: 0.4 cm. Width: 0.1 cm. Shape: Fused into a tube. Apex: Acute. Base: Rounded. Other: There are one or often two very minute sepal-like appendages at the base where the calyx fuses to the peduncle; they are loosely appressed to the calyx tube and are falcate in shape, occasionally being deeply bi-furcated in which case the inside margin of this clefted part is deeply incised, while the outer edge is entire to crenulate; they are closely paired and appear on only one side of the calyx and together are less than one-fourth the width of the circumference of the calyx tube; they are 0.05 cm to 0.1 cm long and 0.001 cm to 0.003 cm wide; there are also occasional 0.5 cm to 0.8 cm long falsate leaves extending at the base where the calyx fuses to the peduncle that can be 0.05 cm to 0.09 cm wide, loose and following the same contour of the calyx at a 20° to 30° angle from the base. Margin: Crenulate. Texture: Upper surface: Papillate with stellate hairs. Lower surface: Papillate. Color: Upper surface: RHS 139D. Lower surface: RHS 139A. Peduncle: Length: About 3.0 cm to 5.0 cm. Diameter: 0.09 cm. Strength: Flexible. Color: RHS 139C. Texture: Very floccose. Pedicel: Length: 0.2 cm. Diameter: 0.1 cm. Color: RHS 139C. Texture: Floccose.

Reproductive organs:

*Stamens.*—Quantity per flower: 4. Filament: Completely fused to inside of corolla tube; cannot determine length or color. Anther: Length: 0.1 cm. Color: RHS 4D. Pollen amount: Moderate. Pollen color: RHS 4D.

*Pistil.*—Quantity per flower: 1. Length: 0.2 cm. Stigma: Shape: Long and clefted. Color: RHS 137C. Style: Length: 0.1 cm. Color: RHS 192B. Ovary: Color: RHS 145A.

Fruit and seed set: Moderate to low. Seeds are elongated football-shaped, 0.1 cm to 0.15 cm long, and RHS 158A in color.

Disease and insect resistance: None observed.

COMPARISON WITH PARENTAL AND COMMERCIAL VARIETY

'Hinebud3' differs from the un-named female *Buddleia* parent (unpatented) in that 'Hinebud3' is shorter than the female parent ('Hinebud3' is about 4 feet or less in height, while the female parent is about 12 to 15 feet in height). Additionally, 'Hinebud3' has white flowers with light yellow centers and a compact plant habit, while the female parent has pink/mauve flowers with orange center and an open and loose plant habit.

'Hinebud3' differs from the male *Buddleia* parent (unpatented) in that 'Hinebud3' is shorter than the male parent ('Hinebud3' is about 4 feet or less in height, while the male parent is about 5 to 6 feet tall). Additionally, 'Hinebud3' has white flowers with light yellow centers, while the male parent has lilac flowers with orange centers.

'Hinebud3' differs from the commercial comparison 'White Profusion' (unpatented) in that 'Hinebud3' is shorter than 'White Profusion' ('Hinebud3' is about 4 feet or less in height, while 'White Profusion' is 15 to 18 feet tall). Additionally, 'Hinebud3'white has white flowers with light yellow eyes, dark green leaves, and a very tight and compact plant habit, while 'White Profusion' has white flowers with yellowish tones and orange eyes, light green leaves, and a loose and large plant habit.

I claim:

1. A new and distinct variety of *Buddleia* plant as shown and described herein.

* * * * *